US012650429B2

(12) United States Patent
Miyazawa et al.

(10) Patent No.: US 12,650,429 B2
(45) Date of Patent: Jun. 9, 2026

(54) ADENOVIRUS IMMUNOASSAY METHOD AND ADENOVIRUS IMMUNOASSAY INSTRUMENT

(71) Applicant: DENKA COMPANY LIMITED, Tokyo (JP)

(72) Inventors: Takashi Miyazawa, Gosen (JP); Miwa Kuwahara, Gosen (JP)

(73) Assignee: DENKA COMPANY LIMITED, Tokyo (JP)

( * ) Notice: Subject to any disclaimer, the term of this patent is extended or adjusted under 35 U.S.C. 154(b) by 906 days.

(21) Appl. No.: 17/918,926

(22) PCT Filed: Apr. 15, 2021

(86) PCT No.: PCT/JP2021/015541
§ 371 (c)(1),
(2) Date: Oct. 14, 2022

(87) PCT Pub. No.: WO2021/210633
PCT Pub. Date: Oct. 21, 2021

(65) Prior Publication Data
US 2024/0053338 A1 Feb. 15, 2024

(30) Foreign Application Priority Data
Apr. 16, 2020 (JP) ................................. 2020-073239

(51) Int. Cl.
*C07K 16/081* (2026.01)
*G01N 33/569* (2006.01)

(52) U.S. Cl.
CPC ..... *G01N 33/56983* (2013.01); *C07K 16/081* (2013.01); *G01N 2333/075* (2013.01); *G01N 2470/04* (2021.08)

(58) Field of Classification Search
CPC ....... G01N 33/56983; G01N 2333/075; G01N 2470/04; C07K 16/081; C07K 2317/33; C07K 16/2803; Y02A 50/30
See application file for complete search history.

(56) References Cited

U.S. PATENT DOCUMENTS

| | | |
|---|---|---|
| 4,487,829 A | 12/1984 | Sharp et al. |
| 11,360,088 B2 | 6/2022 | Inano et al. |

FOREIGN PATENT DOCUMENTS

| | | |
|---|---|---|
| EP | 2 161 285 A1 | 3/2010 |
| JP | 2000-290298 A | 10/2000 |
| JP | 2000-290299 A | 10/2000 |
| JP | 2007-57495 A | 3/2007 |
| JP | 2008-196967 A | 8/2008 |
| JP | 2015-55487 A | 3/2015 |
| WO | WO 2015/015003 A1 | 2/2015 |

OTHER PUBLICATIONS

Extended European Search Report for European Application No. 21789366.8, dated Aug. 4, 2023.
Qiu et al., "Epitope mapping and cross-reactivity analysis of the monoclonal antibodies against hexon protein of human adenovirus type 3," Virus Research, vol. 146, 2009 (Available online Sep. 2, 2009), pp. 58-65.
"Adenovirus Infection", Infectious Agents Surveillance Report, vol. 38, Jul. 14, 2017, pp. 1-2 (3 pages total), with a partial translation.
Adam et al., "Antigenic Relationships Among the Members of Adenovirus Subgenera Determined by Monoclonal Antibodies", Acta Microbiologica Hungarica, vol. 39, No. 3-4, 1992, pp. 309-316 (10 pages total).
International Search Report for International Application No. PCT/ JP2021/015541, dated Jul. 6, 2021, with an English translation.
Japanese Office Action for Japanese Application No. 2020-073239, dated Apr. 1, 2022, with an English translation.
Japanese Office Action for Japanese Application No. 2020-073239, dated Sep. 30, 2022, with an English translation.
Seto et al., "Using the Whole-Genome Sequence to Characterize and Name Human Adenoviruses", Journal of Virology, vol. 85, No. 11, Jun. 2011, pp. 1-2.
Timoshicheva et al., "Use of Hexon as an Antigen for the Production of Monoclonal Antibodies Capable of Detecting Multiple Adenovirus Types", Biologicals, vol. 58, 2019, pp. 44-49.
Written Opinion of the International Searching Authority for International Application No. PCT/JP2021/015541, dated Jul. 6, 2021.

*Primary Examiner* — Rachel B Gill
*Assistant Examiner* — Imma Barrera
(74) *Attorney, Agent, or Firm* — Birch, Stewart, Kolasch & Birch, LLP

(57) ABSTRACT

An object of the present invention is to provide: a monoclonal antibody that makes it possible that adenovirus contained in a test specimen is detected and measured rapidly, simply, and with high-sensitivity; and an immunoassay for adenovirus and an immunoassay device therefor, for both of which the monoclonal antibody is used. The present invention provides: a monoclonal antibody or an antigen-binding fragment thereof, including heavy chains CDR1 to CDR3 as shown in the following (a) to (c) and a light chain CDR1 as shown in the following (d); and an immunoassay and an immunoassay device, for both of which the monoclonal antibody or the antigen-binding fragment thereof is used; (a) a heavy chain CDR1 composed of an amino acid sequence containing NY; (b) a heavy chain CDR2 composed of an amino acid sequence containing SN; (c) a heavy chain CDR3 composed of an amino acid sequence containing SYY and DY; and (d) a light chain CDR1 composed of an amino acid sequence containing NG.

6 Claims, 1 Drawing Sheet
Specification includes a Sequence Listing.

without Reduction Treatment          with Reduction Treatment without Reduction Treatment                    with Reduction Treatment

SEQUENCE LISTING

<160> NUMBER OF SEQ ID NOS: 12

<210> SEQ ID NO 1
<211> LENGTH: 6
<212> TYPE: PRT
<213> ORGANISM: Adenovirus sp.

<400> SEQUENCE: 1

```
Asn Asn Tyr Tyr Trp Asn
1               5

<210> SEQ ID NO 2
<211> LENGTH: 16
<212> TYPE: PRT
<213> ORGANISM: Adenovirus sp.

<400> SEQUENCE: 2

Tyr Ile Lys Tyr Asp Gly Ser Asn Asn Asn Pro Ser Leu Lys Asn
1               5                   10                  15

<210> SEQ ID NO 3
<211> LENGTH: 11
<212> TYPE: PRT
<213> ORGANISM: Adenovirus sp.

<400> SEQUENCE: 3

Arg Ala Ser Tyr Tyr Trp Asp Tyr Phe Asp Val
1               5                   10

<210> SEQ ID NO 4
<211> LENGTH: 11
<212> TYPE: PRT
<213> ORGANISM: Adenovirus sp.

<400> SEQUENCE: 4

Lys Ala Asn Glu Asp Ile Tyr Asn Gly Leu Ala
1               5                   10

<210> SEQ ID NO 5
<211> LENGTH: 7
<212> TYPE: PRT
<213> ORGANISM: Adenovirus sp.

<400> SEQUENCE: 5

Gly Ala Thr Ser Leu Glu Ala
1               5

<210> SEQ ID NO 6
<211> LENGTH: 9
<212> TYPE: PRT
<213> ORGANISM: Adenovirus sp.

<400> SEQUENCE: 6

Gln Gln Tyr Trp Ser Thr Pro Leu Thr
1               5

<210> SEQ ID NO 7
<211> LENGTH: 5
<212> TYPE: PRT
<213> ORGANISM: Adenovirus sp.

<400> SEQUENCE: 7

Asn Tyr Trp Ile His
1               5

<210> SEQ ID NO 8
<211> LENGTH: 17
<212> TYPE: PRT
<213> ORGANISM: Adenovirus sp.

<400> SEQUENCE: 8

Glu Ile Asp Pro Thr Asn Gly Arg Ser Asn Tyr Asn Glu Lys Phe Lys
```

-continued

```
1               5              10             15

Thr

<210> SEQ ID NO 9
<211> LENGTH: 14
<212> TYPE: PRT
<213> ORGANISM: Adenovirus sp.

<400> SEQUENCE: 9

Arg Ser Tyr Tyr Gly Ser Thr Tyr Asp Tyr Gly Leu Asp Tyr
1               5              10

<210> SEQ ID NO 10
<211> LENGTH: 16
<212> TYPE: PRT
<213> ORGANISM: Adenovirus sp.

<400> SEQUENCE: 10

Arg Ser Ser Lys Ser Leu Leu His Leu Asn Gly Asn Thr Tyr Leu Tyr
1               5              10             15

<210> SEQ ID NO 11
<211> LENGTH: 7
<212> TYPE: PRT
<213> ORGANISM: Adenovirus sp.

<400> SEQUENCE: 11

Arg Met Ser Asn Leu Ala Ser
1               5

<210> SEQ ID NO 12
<211> LENGTH: 9
<212> TYPE: PRT
<213> ORGANISM: Adenovirus sp.

<400> SEQUENCE: 12

Val Gln His Leu Glu Tyr Pro Tyr Thr
1               5
```

ADENOVIRUS IMMUNOASSAY METHOD AND ADENOVIRUS IMMUNOASSAY INSTRUMENT

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "0760-0551PUS1_ST25.txt" created on May 31, 2023 and is 2,310 bytes in size. The sequence listing contained in this .txt file is part of the specification and is hereby incorporated by reference herein in its entirety.

TECHNICAL FIELD

The present invention relates to an immunoassay for adenovirus and an immunoassay device therefor, and to an anti-adenovirus antibody for the immunoassay and the device.

BACKGROUND ART

Adenovirus is known as a pathogen of the following: a respiratory disease such as acute febrile pharyngitis, pharyngoconjunctivitis, acute airway inflammation, or viral pneumonia; an eye disease such as acute follicular conjunctivitis or epidemic keratoconjunctivitis; a gastrointestinal disease such as transmissible gastroenteritis; a urologic disease such as urethritis; or the like. At present, adenovirus is classified into seven species A to G, and there are more than 80 types of adenovirus. It has been reported that the types up to type 51 are serotypes, and that the types from type 52 and above are genotypes based on the determination of the entire base sequence (Non-patent Document 1). When humans are infected with adenovirus, the humans can exhibit various clinical symptoms, and do not often exhibit a specific pathological condition, and thus, it is difficult to prove adenovirus infection from a clinical symptom. In addition, adenovirus is very infectious, and preventing herd infection is considered to involve proving viral infection early.

Examples of methods developed to detect adenovirus rapidly and simply include an immunochromatography to be performed with an anti-adenovirus antibody and a method to be performed with EIA. However, in the ophthalmologic field where a specimen can be collected only in a small amount, the positive ratio is 60% or less, and there is a demand for a rapid higher-sensitivity diagnostic method or an anti-adenovirus monoclonal antibody usable for such a method.

The infectious disease surveillance of National Institute of Infectious Diseases provides the information that there are patients who have been found to have pharyngoconjunctival fever, transmissible gastroenteritis, or epidemic keratoconjunctivitis as an adenovirus-associated disease. It is known that acute respiratory disease and pharyngoconjunctival fever are caused by the adenovirus species B, C, and E, that transmissible gastroenteritis is caused by the adenovirus species A, F, and G, and that epidemic keratoconjunctivitis is caused by the adenovirus species B, D, and E (Non-Patent Document 2). The species B adenovirus type 3 and the species E adenovirus type 4 are the most common etiology of epidemic keratoconjunctivitis and pharyngoconjunctival fever, and the species D adenovirus type 8, type 19, and type 37 are also the causes of a serious outbreak of epidemic keratoconjunctivitis in some countries, particularly in East Asia and Southeast Asia. Adenovirus type 8, type 19, and type 37 are well known as the epidemiologic causes of nosocomial infection. Nosocomial infection induced by adenovirus has recently posed a notable social issue in public hygiene and an economical and ethical issue in hospitals.

Up to now, a plurality of monoclonal antibodies that react with adenovirus have been produced and reported. For example, disclosed is a method in which adenovirus is detected using a monoclonal antibody that reacts with a specific subtype of adenovirus (Patent Documents 1 and 2).

PRIOR ART DOCUMENTS

Non-Patent Documents

[Non-patent Document 1] Seto D, et al., J Virol 85: 5701-5702, 2011

[Non-patent Document 2] IASR Vol. 38, p.133-135: July 2017

[Patent Document 1] JP 2000-290298 A

[Patent Document 2] JP 2000-290299 A

SUMMARY OF THE INVENTION

Problems to be Solved by the Invention

However, none of the monoclonal antibodies for adenovirus that are currently produced have sufficient detection sensitivity for adenovirus, and there is a demand for a monoclonal antibody that reacts with higher sensitivity.

An object of the present invention is to provide: a monoclonal antibody that makes it possible that adenovirus contained in a test specimen is detected and measured rapidly, simply, and with high-sensitivity; and an immunoassay for adenovirus and an immunoassay device therefor, for both of which the monoclonal antibody is used.

Means for Solving the Problems

As a result of intensive study on the above-mentioned problems, the present inventors have discovered a specific monoclonal antibody that reacts with adenovirus with high sensitivity, and have thereby completed the present invention. That is, the present invention is as follows.

[1] A monoclonal antibody or an antigen-binding fragment thereof, including heavy chains CDR1 to CDR3 as shown in the following (a) to (c) and a light chain CDR1 as shown in the following (d):

(a) a heavy chain CDR1 composed of an amino acid sequence containing NY;

(b) a heavy chain CDR2 composed of an amino acid sequence containing SN;

(c) a heavy chain CDR3 composed of an amino acid sequence containing SYY and DY; and (d) a light chain CDR1 composed of an amino acid sequence containing NG.

[2] The monoclonal antibody or the antigen-binding fragment thereof according to [1], including heavy chains CDR1 to CDR3 as shown in the following (a-1) to (c-1) and light chains CDR1 to CDR3 as shown in the following (d-1) to (f-1):

(a-1) a heavy chain CDR1 composed of an amino acid sequence containing (SEQ ID NO: 1)

NNYYWN;

(b-1) a heavy chain CDR2 composed of an amino acid sequence containing (SEQ ID NO: 2)

YIKYDGSNNNNPSLKN;

(c-1) a heavy chain CDR3 composed of an amino acid sequence containing (SEQ ID NO: 3)

RASYYWDYFDV;

(d-1) a light chain CDR1 composed of an amino acid sequence containing (SEQ ID NO: 4)

KANEDIYNGLA;

(e-1) a light chain CDR2 composed of an amino acid sequence containing (SEQ ID NO: 5)

GATSLEA;

and (f-1) a light chain CDR3 composed of an amino acid sequence containing (SEQ ID NO: 6)

QQYWSTPLT.

[3] The monoclonal antibody or the antigen-binding fragment thereof according to [1], including heavy chains CDR1 to CDR3 as shown in the following (a-2) to (c-2) and light chains CDR1 to CDR3 as shown in the following (d-2) to (f-2):

(a-2) a heavy chain CDR1 composed of an amino acid sequence containing (SEQ ID NO: 7)

NYWIH;

(b-2) a heavy chain CDR2 composed of an amino acid sequence containing (SEQ ID NO: 8)

EIDPTNGRSNYNEKFKT;

(c-2) a heavy chain CDR3 composed of an amino acid sequence containing (SEQ ID NO: 9)

RSYYGSTYDYGLDY;

(d-2) a light chain CDR1 composed of an amino acid sequence containing (SEQ ID NO: 10)

RSSKSLLHLNGNTYLY;

(e-2) a light chain CDR2 composed of an amino acid sequence containing (SEQ ID NO: 11)

RMSNLAS;

and (f-2) a light chain CDR3 composed of an amino acid sequence containing (SEQ ID NO: 12)

VQHLEYPYT.

[4] The monoclonal antibody or the antigen-binding fragment thereof according to any one of [1] to [3], having an identity of at least 60% or more with each of the amino acid sequences contained in the heavy chains CDR1 to CDR3 and/or the light chains CDR1 to CDR3.

[5] An immunoassay for adenovirus, including performing the immunoassay of adenovirus by using antigen-antibody reaction between the monoclonal antibody or the antigen-binding fragment thereof according to any one of [1] to [4] and adenovirus in a sample.

[6] The immunoassay according to [5], wherein the immunoassay is a sandwich method, and the monoclonal antibody or the antigen-binding fragment thereof is used as at least any one of a label or a solid phase.

[7] An immunoassay device for adenovirus, including the monoclonal antibody or the antigen-binding fragment thereof according to any one of [1] to [4].

Effects of the Invention

The present invention can provide: a monoclonal antibody that makes it possible that adenovirus contained in a test specimen is detected and measured rapidly, simply, and with high-sensitivity; and an immunoassay for adenovirus and an immunoassay device therefor, for both of which the monoclonal antibody is used.

MODE FOR CARRYING OUT THE INVENTION

Figure 1:
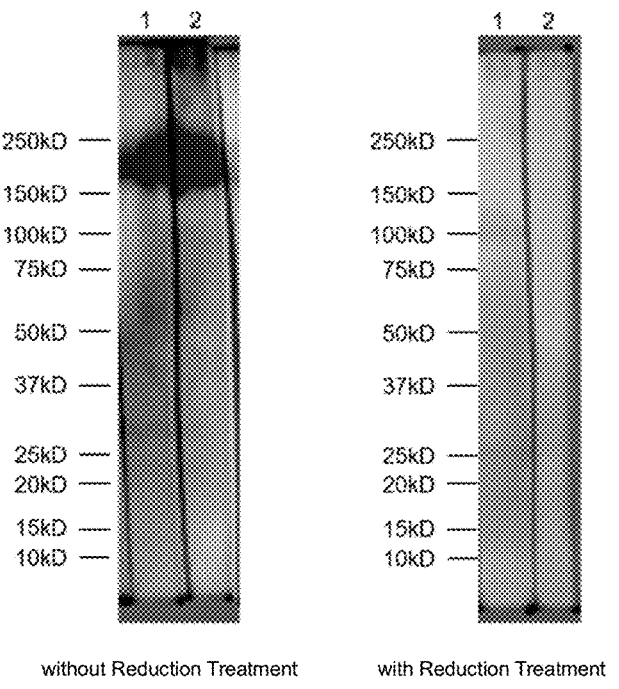
FIG. 1 is a diagram illustrating the results of Western blotting performed in Example 3.

Below, embodiments of the present invention will be described in detail.

<Monoclonal Antibody or Antigen-binding Fragment Thereof>

A monoclonal antibody or an antigen-binding fragment thereof according to the present invention is specifically bound to adenovirus, and includes heavy chains CDR1 to CDR3 as shown in the following (a) to (c) and a light chain CDR1 as shown in the following (d):

(a) a heavy chain CDR1 composed of an amino acid sequence containing NY;

(b) a heavy chain CDR2 composed of an amino acid sequence containing SN;

(c) a heavy chain CDR3 composed of an amino acid sequence containing SYY and DY; and (d) a light chain CDR1 composed of an amino acid sequence containing NG.

A monoclonal antibody or an antigen-binding fragment thereof according to the present invention has a basic structure composed of a heavy chain and a light chain, and the heavy chain and the light chain have the respective variable regions that can specifically bind to an antigen. $V_H$ refers to the variable region of the heavy chain, and $V_L$ refers to the variable region of the light chain. The variable region of the heavy chain and that of the light chain each contain amino acid sequences of complementarity-determining regions (CDR), that is, CDR1, CDR2, and CDR3, and a framework region (FR). For example, the variable region contains three or four FRs (for example, FR1, FR2, FR3, and optionally FR4) together with the three CDRs.

Examples of a monoclonal antibody of the present invention include quadruple-chain antibodies (for example, having two light chains and two heavy chains), recombinant antibodies, or modified antibodies (for example, chimeric antibodies, humanized antibodies, human antibodies, CDR transplanted antibodies, primatized antibodies, deimmunized antibodies, synhumanized (synhumanized) antibodies, half antibodies, and bispecific antibodies). The class of the monoclonal antibody is not limited to IgG, and may also be IgM or IgY.

In the present invention, an antigen-binding fragment of a monoclonal antibody is a fragment that is an antigen-binding site alone separated from the monoclonal antibody. Examples of such a fragment include fragments having specific antigen-binding capacity, such as Fab, Fab', F(ab')2, and single-chain antibodies (scFv) prepared by known methods.

To produce such an antigen-binding fragment, a preparation method known to those skilled in the art can be used. Examples of such a method include: a method in which an antibody is digested with protease (for example, pepsin, papain, or the like) by a conventional method, and then purified by a known method of separating/purifying protein; a preparation method based on genetic recombination; and the like.

As the monoclonal antibody or the antigen-binding fragment thereof according to the present invention, the following antibody 1 or antibody 2 or an antigen-binding fragment thereof is preferable from the viewpoint of the ability to detect adenovirus with higher sensitivity.

(Antibody 1 or Antigen-binding Fragment Thereof)

A monoclonal antibody or an antigen-binding fragment thereof, which includes heavy chains CDR1 to CDR3 as shown in the following (a-1) to (c-1) and light chains CDR1 to CDR3 as shown in the following (d-1) to (f-1):

(a-1) a heavy chain CDR1 composed of an amino acid sequence containing (SEQ ID NO: 1)
NNYYWN;

(b-1) a heavy chain CDR2 composed of an amino acid sequence containing (SEQ ID NO: 2)
YIKYDGSNNNNPSLKN;

(c-1) a heavy chain CDR3 composed of an amino acid sequence containing (SEQ ID NO: 3)
RASYYWDYFDV;

(d-1) a light chain CDR1 composed of an amino acid sequence containing (SEQ ID NO: 4)
KANEDIYNGLA;

(e-1) a light chain CDR2 composed of an amino acid sequence containing (SEQ ID NO: 5)
GATSLEA;

(f-1) a light chain CDR3 composed of an amino acid sequence containing (SEQ ID NO: 6)
QQYWSTPLT.

(Antibody 2 or Antigen-Binding Fragment Thereof)

A monoclonal antibody or an antigen-binding fragment thereof, which includes heavy chains CDR1 to CDR3 as shown in the following (a-2) to (c-2) and light chains CDR1 to CDR3 as shown in the following (d-2) to (f-2):

(a-2) a heavy chain CDR1 composed of an amino acid sequence containing (SEQ ID NO: 7)
NYWIH;

(b-2) a heavy chain CDR2 composed of an amino acid sequence containing (SEQ ID NO: 8)
EIDPTNGRSNYNEKFKT;

(c-2) a heavy chain CDR3 composed of an amino acid sequence containing (SEQ ID NO: 9)
RSYYGSTYDYGLDY;

(d-2) a light chain CDR1 composed of an amino acid sequence containing (SEQ ID NO: 10)
RSSKSLLHLNGNTYLY;

(e-2) a light chain CDR2 composed of an amino acid sequence containing (SEQ ID NO: 11)
RMSNLAS;

and (f-2) a light chain CDR3 composed of an amino acid sequence containing (SEQ ID NO: 12)
VQHLEYPYT.

Examples of a monoclonal antibody or an antigen-binding fragment thereof according to the present invention include such an antibody or a fragment thereof that has a sequence identity of 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, or 99% or more to each of the amino acid sequences contained in the heavy chains CDR1 to CDR3 and/or the light chains CDR1 to CDR3 of each of the antibody 1 and the antibody 2.

(Method of Preparing Monoclonal Antibody)

The monoclonal antibody of the present invention may be obtained by immunizing an animal with a complex or an extract containing adenovirus as an antigen of interest or with the adenovirus or a partial peptide thereof by a known immunological method, and then preparing a hybridoma using cells of the immunized animal. The length of the peptide used for the immunization is not limited. Preferably, a peptide of not less than 5 amino acids, more preferably not less than 10 amino acids, may be used to provide the immunogen.

The immunogen can be obtained from a culture liquid, or can be obtained by incorporating DNA encoding an arbitrary adenovirus antigen into a plasmid vector, and introducing the resulting vector to a host cell, followed by allowing expression of the adenovirus. Alternatively, such an arbitrary adenovirus antigen or the partial peptide thereof to be used as the immunogen can be expressed as a fusion protein with a protein exemplified below, and the expressed fusion protein can be used as the immunogen after purification or without purification. The preparation of the fusion protein can be carried out using, for example, Glutathion S-transferase (GST), maltose-binding protein (MBP), thioredoxin (TRX), Nus-tag, S-tag, HSV-tag, FRAG tag, polyhistidine tag, or the like which is commonly used as a "protein expression/purification tag" by those skilled in the art. Preferably, the fusion protein with such a protein is cleaved into the portion of the arbitrary adenovirus antigen or the partial peptide thereof, and the tag portion, using a digestive enzyme, and subjected to separation/purification before use as the immunogen.

The preparation of the monoclonal antibody from the immunized animal can be easily carried out by the well-known method of Kohler et al. (Kohler et al., Nature, vol. 256, p. 495-497 (1975)). That is, antibody-producing cells such as spleen cells or lymphocytes are recovered from the immunized animal, and the recovered cells are fused with mouse myeloma cells by a conventional method to prepare hybridomas. The resulting hybridomas are cloned by the limiting dilution method or the like. Thereafter, a monoclonal antibody that undergoes antigen-antibody reaction with the antigen used for the immunization of the animal is selected from the monoclonal antibodies produced by the cloned hybridomas.

Purification of the monoclonal antibody from ascites or a culture supernatant may be carried out by a known immunoglobulin purification method. Examples of the method include fractionation by salting out using ammonium sulfate or sodium sulfate, PEG fractionation, ethanol fractionation, DEAE ion-exchange chromatography, and gel filtration. Depending on the species of the immunized animal and the class of the monoclonal antibody, affinity chromatography using a carrier to which any of protein A, protein G, and protein L is bound may be used for the purification.

<Immunoassay>

In the present invention, using the above-mentioned monoclonal antibody or an antigen-binding fragment thereof makes it possible to detect adenovirus with very high sensitivity. In the following description preceding the Examples section, a "monoclonal antibody" means a "monoclonal antibody or an antigen-binding fragment thereof", unless otherwise obvious from the context.

In the present invention, adenovirus is detected by performing an immunoassay of adenovirus using antigen-antibody reaction between the above-mentioned monoclonal antibody and adenovirus in a sample. That a monoclonal antibody undergoes antigen-antibody reaction with adenovirus means that a monoclonal antibody reacts specifically with adenovirus. The term "specific" means that, in a liquid system containing a mixture of antigen proteins and the monoclonal antibody, the antibody does not cause antigen-antibody reaction with components other than the antigen proteins at a detectable level, or, even in cases where the antibody causes a certain binding reaction or association reaction with such a component, the reaction is evidently weaker than the antigen-antibody reaction between the antibody and the antigen proteins.

In the present invention, examples of immunoassays that can be used include any method well known to those skilled in the art, such as a competition method, condensation method, Western blotting, immunostaining method, sandwich method, and the like.

A sandwich method is preferable as an immunoassay in the present invention. The sandwich method per se is well known in the field of immunoassays, and can be carried out by, for example, immunochromatography or ELISA. These sandwich methods per se are well known, and the method of the present invention can be carried out in the same manner as a well-known sandwich method except that the above-mentioned specific monoclonal antibody is used.

In a sandwich method, two kinds of antibodies (an immobilized antibody immobilized in a solid phase and a labeled antibody) that recognize an antigen are used. In a method of the present invention, at least any one of these two kinds of antibodies is the above-mentioned monoclonal antibody of the present invention. In the case of the immobilized antibody immobilized in a solid phase, the amount of the antibody that can be immobilized per unit area is limited. To better achieve that object of the present invention which is to enhance the sensitivity, a monoclonal antibody according to the present invention is preferably used at least for the immobilized antibody. In cases where at least two antigens to be recognized by the monoclonal antibody are present in a single molecule or a single complex, the monoclonal antibody of a single kind can be used as a solid-phased antibody and a labelled antibody to perform a sandwich method.

In the immunoassay based on the detection principle of a sandwich method, any solid phase may be used as the solid phase on which the antibody is to be immobilized, as long as the antibody can be immobilized thereon by a known technique. The solid phase may be arbitrarily selected from known solid phases such as porous thin films (membranes) having a capillary action; particles, test tubes, and resin plates. Examples of the substance for labeling the antibody include enzymes, radioisotopes, fluorescent substances, luminescent substances, colored particles, and colloidal particles. Among the above-mentioned immunoassay methods using various materials, lateral-flow immunoassay methods using a membrane are preferred from the viewpoint of enabling simple and rapid clinical tests.

In cases where adenovirus is quantified or semi-quantified using the monoclonal antibody in the present invention, such quantification or semi-quantification involves "measurement" inevitably, and thus, is included in the "measurement" in the present invention. That is, in the present invention, "measurement" in an immunoassay includes any of quantification, semi-quantification, and detection.

EXAMPLES

The present invention is described below by way of Examples. However, the present invention is not limited to the following Examples.

Example 1

Preparation of Anti-adenovirus Monoclonal Antibody

1. Preparation of Adenovirus Antigen

Adenovirus was allowed to infect mammalian cells sensitive thereto. The resulting cells were cultured for some days. Then, the culture liquid of the adenovirus-infected cells were inactivated by ultraviolet irradiation and made ready for use.

2. Preparation of Anti-Adenovirus Monoclonal Antibody

BALB/c mice were immunized with the adenovirus-inactivated antigen prepared in 1, and kept for a certain period. From each mouse, the spleen was removed, and fusion with mouse myeloma cells (P3×63) was carried out by the method of Kohler et al. (Kohler et al., Nature, vol. 256, p. 495-497 (1975)) to obtain a plurality of hybridoma cell lines that produce anti-adenovirus antibodies.

The obtained cell line was intraperitoneally administered to pristane-treated BALB/c mice. About two weeks later, antibody-containing ascites was collected. From the ascites obtained, IgG was purified by affinity chromatography using a protein A column, to obtain a plurality of purified anti-adenovirus monoclonal antibodies.

In the below-mentioned Examples, two antibodies, an antibody 1 and an antibody 2, were used, which were selected from a plurality of the resulting anti-adenovirus monoclonal antibodies, considering reactivity and specificity.

Example 2

Immunoassay Device for Measuring Adenovirus

1. Immobilization of Anti-adenovirus Antibody on Nitrocellulose Membrane

The anti-adenovirus antibody (antibody 2) prepared in Example 1 was diluted with a buffer. The resulting liquid and an anti-mouse IgG antibody were made ready for use. The anti-adenovirus antibody and the anti-mouse IgG antibody were linearly applied respectively to the sample pad side and the absorber side of a nitrocellulose membrane lined with a PET film. Then, the nitrocellulose membrane was dried sufficiently under warm air to obtain a membrane having an anti-adenovirus antibody immobilized thereon.

2. Immobilization of Anti-adenovirus Antibody on Colored Polystyrene Particles

The anti-adenovirus antibody (antibody 1) prepared in Example 1 was covalently bound to colored polystyrene particles, and the colored polystyrene particles were suspended in a suspension. Then, colored polystyrene particles to which the anti-adenovirus antibodies were bound and which were dispersed sufficiently by ultrasonication were obtained. In the present description, the particles obtained here are referred to as "anti-adenovirus antibody-immobilized particles".

3. Application/Drying of Colored Polystyrene Particles to Which Anti-Adenovirus Antibody is Bound A predetermined amount of the anti-adenovirus antibody-immobilized particles prepared in 2 were applied to a glass-fiber non-woven fabric, and the non-woven fabric was then dried sufficiently under warm air. In the present description, the pad obtained here is referred to as a "labeled antibody pad".

4. Production of Adenovirus Test Device

The anti-adenovirus antibody-immobilized membrane prepared in 1 and the labelled antibody pads prepared in 2 and 3 were laminated with other members (backing sheet, absorption zone, and sample pad), and the resulting laminate was cut into a piece with a width of 5 mm, to provide an adenovirus test device.

5. Confirmation of Reactivity of Adenovirus Test Device

A culture liquid of adenovirus-infected cells of each type was diluted with a buffer to prepare a two-fold dilution series of each type of adenovirus.

The adenovirus diluted liquid prepared was added to a sample suspension (10 mM Tris (pH 8.0), 1 w/v % polyoxyethylene octylphenyl ether, 3 w/v% arginine, and 3 w/v % BSA), and 50 µL of the resulting mixture was added dropwise to the adenovirus test device produced in 4. Then, the test device was left to stand for 5 minutes.

In cases where coloring could be visually observed at both the position where the anti-mouse IgG antibody was applied and the position where the anti-adenovirus antibody was applied, the test result was evaluated as + (positive). In cases where coloring could be visually observed only at the position where the anti-mouse IgG antibody was applied and where coloring could not be visually observed at the position where the anti-adenovirus antibody was applied, the test result was evaluated as − (negative). In cases where coloring could not be visually observed at the position where the anti-mouse IgG antibody was applied, the test result was evaluated as invalid.

The lowest adenovirus concentration at which the test result was evaluated as positive was regarded as the lowest detection sensitivity. The results are shown in Table 1.

TABLE 1

| | Adenovirus | Lowest Detection Sensitivity | |
| --- | --- | --- | --- |
| Type | Species | TCID$_{50}$/Test | copies/Test |
| 1 | C | $1.95 \times 10^2$ | $2.50 \times 10^3$ |
| 2 | C | $1.95 \times 10^2$ | $6.25 \times 10^3$ |
| 3 | B | $2.79 \times 10^2$ | $1.25 \times 10^4$ |
| 5 | C | $7.85 \times 10^1$ | $6.25 \times 10^3$ |
| 6 | C | $5.58 \times 10^2$ | $3.13 \times 10^3$ |
| 7 | B | $1.74 \times 10^2$ | $1.25 \times 10^4$ |
| 8 | D | $1.95 \times 10^1$ | $1.25 \times 10^3$ |
| 11 | B | $2.79 \times 10^2$ | $5.00 \times 10^4$ |
| 19 | D | $2.44 \times 10^1$ | $1.25 \times 10^4$ |
| 31 | A | $4.48 \times 10^2$ | $1.25 \times 10^5$ |
| 37 | D | $3.14 \times 10^1$ | $2.50 \times 10^3$ |

As shown in Table 1, it was possible to confirm that the immunoassay device used with the anti-adenovirus antibody of the present invention reacted with many types of adenovirus belonging to the species A to D.

In addition it was possible to confirm that the device reacted with each of the subtypes: type 53, type 54, type 56, type 64, type 79, type 81, and type 85.

6. Confirmation of Specificity of Adenovirus Test Device

To the adenovirus test device produced in 4, 50 µL of a sample suspension containing virus that induces respiratory infection was added dropwise, and the test device was left to stand for 5 minutes.

In cases where coloring could be visually observed at both the position where the anti-mouse IgG antibody was applied and the position where the anti-adenovirus antibody was applied, the test result was evaluated as +. In cases where coloring could be visually observed only at the position where the anti-mouse IgG antibody was applied and where coloring could not be visually observed at the position where the anti-adenovirus antibody was applied, the test result was evaluated as −. In cases where coloring could not be visually observed at the position where the anti-mouse IgG antibody was applied, the test result was evaluated as invalid.

The results are shown in Table 2.

TABLE 2

| Virus | Measurement Results |
| --- | --- |
| Coxsackievirus type A9 | — |
| Coxsackievirus type B4 | — |
| Coxsackievirus type B5 | — |
| Coxsackievirus type B6 | — |
| Echo virus type 2 | — |
| Echo virus type 3 | — |
| Echo virus type 4 | — |
| Echo virus type 6 | — |
| Echo virus type 9 | — |
| Echo virus type 11 | — |
| Echo virus type 30 | — |
| Herpes simplex virus type 1 | — |
| Human Metapneumovirus type A | — |
| Human Metapneumovirus type B | — |
| Influenza virus A/New Caledonia/20/99 (H1N1) | — |
| Influenza virus A/Beijing/262/95 (H1N1) | — |
| Influenza virus A/New York/55/2004 (H3N2) | — |
| Influenza virus A/Hiroshima/52/2005 (H3N2) | — |
| Influenza virus B/Shanghai/361/2002 (Yamagata) | — |
| Influenza virus B/Malaysia/2506/2004 (Victoria) | — |
| Measles virus | — |
| Mumps virus | — |
| Parainfluenza virus type 1 | — |
| Parainfluenza virus type 2 | — |
| Parainfluenza virus type 3 | — |
| Parainfluenza virus type 4 | — |
| RS virus Long strain (type A) | — |
| RS virus CH-18 strain (type B) | — |

As shown in Table 2, it was possible to confirm that the adenovirus immunoassay device used with the anti-adenovirus antibody of the present invention reacted specifically with adenovirus, because the immunoassay device reacted with adenovirus, but exhibited no crossreactivity with the etiological virus of any other respiratory infection.

7. Performance Comparison of Adenovirus Test Device

The lowest detection sensitivity was compared between the adenovirus test device (the present device) prepared in 4 and a commercially available adenovirus kit.

Culture liquids of adenovirus-infected cells were each diluted with a buffer to prepare two-fold dilution series. To the present device, 50 μL of a sample suspension containing an adenovirus diluted liquid was added dropwise, and the present device was left to stand for 5 minutes and evaluated. The commercially available kit was used with a prescribed amount of adenovirus diluted liquid as a sample, and the test result was evaluated by performing a test in accordance with the document attached to each kit.

Assuming that the largest adenovirus dilution ratio at which the test result was evaluated as positive with the present device is "1", the largest dilution ratio at which the test result was evaluated as positive with a commercially available adenovirus kit was regarded as relative sensitivity, and is shown in Table 3.

TABLE 3

| | Relative Sensitivity of Each Type (Species)[1] | | | | | | |
| --- | --- | --- | --- | --- | --- | --- | --- |
| Kit | Type 1 (C) | Type 2 (C) | Type 3 (B) | Type 4 (E) | Type 11 (B) | Type 37 (D) | Type 54 (D) |
| Present Kit | 1 | 1 | 1 | 1 | 1 | 1 | 1 |
| Kit A | 1 | ½ | 1 | 1 | 1 | 1 | 1 |
| Kit B | ½ | ¼ | ½ | ½ | ½ | ½ | ¼ |
| Kit C | ⅛ | ⅛ | ⅛ | 1/20 | 1/20 | NT | NT |
| Kit D | 1 | ½ | ½ | ½ | ½ | ½ | ½ |
| Kit E | 1/16 | 1/32 | 1/100 | 1/80 | 1/400 | NT | NT |
| Kit F | ½ | ¼ | ½ | ½ | ½ | ½ | ¼ |
| Kit G | ¼ | ⅛ | ⅛ | ⅛ | ¼ | ¼ | ¼ |
| Kit H | ⅛ | ¼ | ¼ | ¼ | ¼ | ¼ | ¼ |

NT: Not tested

As shown in Table 3, it was possible to confirm that the immunoassay device used with the anti-adenovirus antibody of the present invention had the highest reactivity with adenovirus type 2, and also had the highest reactivity with another type of adenovirus in the same manner as the kit A did.

Example 3

Antigen Recognition Site of Anti-Adenovirus Monoclonal Antibody

The antigen recognition site of the anti-adenovirus monoclonal antibody obtained in Example 1 was verified by Western blotting and LC-MS/MS.

1. Preparation of Concentrated-Adenovirus Liquid

Adenovirus was allowed to infect A549 cells, and cultured. On culture day 7, the adenovirus-infected cells were recovered and disrupted by ultrasonication. Cell residues were removed from the disrupted-cell liquid by centrifugation to obtain a concentrated-adenovirus liquid.

2. Preparation of Sample without Reduction Treatment A two-fold dilution series of the concentrated-adenovirus liquid obtained in 1 was prepared, and supplemented with reagents having the respective final concentrations: 62.5 mM Tris-HCl (pH 6.5), 10 w/v % glycerol, 2.3 w/v % SDS, and 0.05% BPB (dye). The resulting mixture was subjected to a conventional method SDS-PAGE without being thermally denatured.

3. Preparation of Sample with Reduction Treatment

A two-fold dilution series of the concentrated-adenovirus liquid obtained in 1 was prepared, and supplemented with reagents having the respective final concentrations: 62.5 mM Tris-HCl (pH 6.5), 10 w/v % glycerol, 2.3 w/v % SDS, 0.05% BPB (dye), and 5% 2-mercaptoethanol. After being thermally denatured at 95° C. for 1 minute, the resulting mixture was subjected to a conventional method SDS-PAGE.

4. Western Blotting

The gels electrophoresed in 2 and 3 were transferred to a PVDF membrane. After blocking of the membrane using skim milk, the membrane was sufficiently washed with PBS-Tween. The membrane was then allowed to react with the anti-adenovirus antibody whose concentration was adjusted to 3.8 μg/mL using PBS-Tween, at room temperature for 1 hour. After sufficiently washing the membrane with PBS-Tween, the membrane was allowed to react with a 3000-fold diluted HRP-labeled anti-mouse antibody at room temperature for 1 hour. After sufficiently washing the membrane with PBS-Tween, signals were detected using a chemiluminescence detection reagent.

The results of Western Blotting are shown in FIG. 1.

A shown in FIG. 1, two antibodies (the antibody 1 and the antibody 2) produced in Example 1 reacted strongly with the approximately 200 kD protein (hexon trimer) contained in the sample obtained in 2 (without reduction treatment) (the left diagram). It is considered that the reduction treatment caused the hexon trimer to become a monomer, and it was recognized that the sample obtained in 3 (with reduction treatment) reacted very weakly with the approximately 100 kD protein (hexon monomer) (right diagram).

Figure 2:
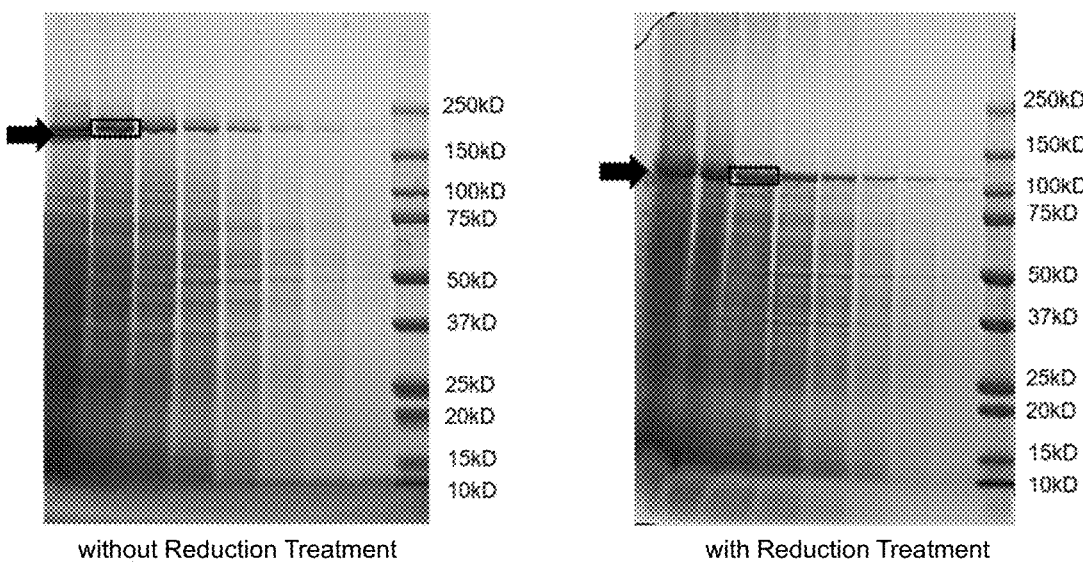
FIG. 2 is a diagram illustrating the results obtained by staining, with CBB, the gel electrophoresed in Example 3.

The results obtained by staining, with CBB, the gels electrophoresed in 2 and 3 are shown in FIG. 2.

As shown by the arrow in FIG. 2, the main protein contained in the sample obtained in 2 (without reduction treatment) was found at approximately 200 kD (the left diagram), and that contained in the sample obtained in 3 (with reduction treatment) was found at 100 to 150 kD (the right diagram). Each stained region denoted by a rectangle in the diagram was cut out, then hydrolyzed with trypsin, and analyzed by LC-MS/MS to give an amino acid sequence. The peptide fragment obtained was analyzed using Mascot (Ver. 2.5) (from Matrix Science Inc.) and Scaffold (from Proteome Software, Inc.), resulting in revealing that both of the stained regions contained a hexon protein of adenovirus as a main constituent.

FIG. 1 and FIG. 2 have revealed that both of the two antibodies obtained in Example 1 reacted more strongly with a protein of a hexon trimer than with a protein of a hexon monomer, and reacted weakly with a monomeric hexon protein.

Example 4

Analysis of Variable Region of Anti-Adenovirus Monoclonal Antibody

1. Base Sequence Analysis of Variable Region of Anti-adenovirus Antibody

The hybridoma cell lines produced in Example 1 to produce the anti-adenovirus antibodies 1 and 2 were sent to Perseus Proteomics Inc., which was requested to make a base sequence analysis of the variable regions of the antibodies. At Perseus Proteomics Inc., RNAs were extracted from the hybridoma cell lines. The amplified products of the variable regions of the anti-adenovirus antibodies were obtained by PCR, and base sequences were obtained from the amplified products.

s2. Amino Acid Sequence Prediction of Variable Region of Anti-adenovirus Antibody From the base sequence information obtained in 1, the amino acid sequences of the variable regions were predicted using a Kabat numbering system. The results are shown in Table 4.

TABLE 4

| Antibody 1 | Heavy Chain | CDR1 Sequence | NNYYWN | SEQ ID NO: 1 |
| | | CDR2 Sequence | YIKYDGSNNNNPSLKN | SEQ ID NO: 2 |
| | | CDR3 Sequence | RASYYWDYFDV | SEQ ID NO: 3 |
| | Light Chain | CDR1 Sequence | KANEDIYNGLA | SEQ ID NO: 4 |
| | | CDR2 Sequence | GATSLEA | SEQ ID NO: 5 |
| | | CDR3 Sequence | QQYWSTPLT | SEQ ID NO: 6 |
| Antibody 2 | Heavy Chain | CDR1 Sequence | NYWIH | SEQ ID NO: 7 |
| | | CDR2 Sequence | EIDPTNGRSNYNEKFKT | SEQ ID NO: 8 |
| | | CDR3 Sequence | RSYYGSTYDYGLDY | SEQ ID NO: 9 |
| | Light Chain | CDR1 Sequence | RSSKSLLHLNGNTYLY | SEQ ID NO: 10 |
| | | CDR2 Sequence | RMSNLAS | SEQ ID NO: 11 |
| | | CDR3 Sequence | VQHLEYPYT | SEQ ID NO: 12 |

From the result of Table 4, it is understood that the sequences common between the antibody 1 and the antibody 2 exist as follows: NY in the heavy chain CDR1, SN in the heavy chain CDR2, SYY and DY in the heavy chain CDR3, and NG in the light chain CDR1. Accordingly, a monoclonal antibody or an antigen-binding fragment thereof according to the present invention which has these common sequences makes it possible to detect adenovirus with much higher sensitivity than a conventional known anti-adenovirus antibody.

Sequence Listing

The invention claimed is:

1. A monoclonal antibody or an antigen-binding fragment, thereof, comprising heavy chains CDR1 to CDR3 as shown in the following (a-1) to (c-1) and light chains CDR1 to CDR3 as shown in the following (d-1) to (f-1):

(a-1) a heavy chain CDR1 consisting of an amino acid sequence of SEQ ID NO: 1;

(b-1) a heavy chain CDR2 consisting of an amino acid sequence of SEQ ID NO: 2;

(c-1) a heavy chain CDR3 consisting of an amino acid sequence of SEQ ID NO: 3;

(d-1) a light chain CDR1 consisting of an amino acid sequence of SEQ ID NO: 4;

(e-1) a light chain CDR2 consisting of an amino acid sequence of SEQ ID NO: 5; and (f-1) a light chain CDR3 consisting of an amino acid sequence of SEQ ID NO: 6.

2. A monoclonal antibody or an antigen-binding fragment thereof, comprising heavy chains CDR1 to CDR3 as shown in the following (a-2) to (c-2) and light chains CDR1 to CDR3 as shown in the following (d-2) to (f-2):

(a-2) a heavy chain CDR1 consisting of an amino acid sequence of SEQ ID NO: 7;

(b-2) a heavy chain CDR2 consisting of an amino acid sequence of SEQ ID NO: 8;

(c-2) a heavy chain CDR3 consisting of an amino acid sequence of SEQ ID NO: 9;

(d-2) a light chain CDR1 consisting of an amino acid sequence of SEQ ID NO: 10;

(e-2) a light chain CDR2 consisting of an amino acid sequence of SEQ ID NO: 11; and (f-2) a light chain CDR3 consisting of an amino acid sequence containing of SEQ ID NO: 12.

3. An immunoassay method for detecting an adenovirus, comprising performing the immunoassay of the adenovirus by using an antigen-antibody reaction between the monoclonal antibody or the antigen-binding fragment thereof according to claim 1 and adenovirus in a sample.

4. The immunoassay method according to claim 3, wherein the immunoassay is a sandwich method, and the monoclonal antibody or the antigen-binding fragment thereof is immobilized on a solid phase and/or is labeled for use in a sandwich immunoassay.

5. An immunoassay device for adenovirus, comprising the monoclonal antibody or the antigen-binding fragment thereof according to claim 1.

6. An immunoassay method for detecting an adenovirus, comprising performing the immunoassay of the adenovirus by using an antigen-antibody reaction between the monoclonal antibody or the antigen-binding fragment thereof according to claim 2 and adenovirus in a sample.

\* \* \* \* \*